United States Patent
Tarsia

Patent Number: 6,106,124
Date of Patent: Aug. 22, 2000

[54] SELF-CONTAINED PHOTO STUDIO LIGHTING APPARATUS

[76] Inventor: Joseph Tarsia, 122 Hoffman St., Valley Stream, N.Y. 11580

[21] Appl. No.: 08/880,130

[22] Filed: Jun. 20, 1997

Related U.S. Application Data

[60] Provisional application No. 60/020,135, Jun. 20, 1996.

[51] Int. Cl.[7] .................................. G03B 15/06
[52] U.S. Cl. .................... 362/6; 362/11; 362/17; 362/126; 362/294; 362/307; 396/4; 396/5
[58] Field of Search ................ 396/1–5; 362/3, 362/6, 8, 11, 16–18, 126, 153, 33, 35, 294, 373, 145, 149, 150, 307

[56] References Cited

U.S. PATENT DOCUMENTS

| | | | |
|---|---|---|---|
| 1,379,949 | 5/1921 | Wedmark | 396/4 |
| 1,447,475 | 3/1923 | Jones | 396/4 |
| 3,690,242 | 9/1972 | Cruichshank | 396/24 |
| 3,952,322 | 4/1976 | Wolfe | 396/4 |
| 4,292,662 | 9/1981 | Gasperini | 362/17 |
| 4,372,659 | 2/1983 | Ogawa | 396/5 |
| 4,475,146 | 10/1984 | Wally, Jr. | 362/11 |
| 4,627,697 | 12/1986 | Second | 396/3 |
| 4,771,305 | 9/1988 | Potoroka | 396/1 |
| 5,067,049 | 11/1991 | Milaire | 362/18 |
| 5,077,640 | 12/1991 | Butler, Jr. | 362/11 |
| 5,113,207 | 5/1992 | Huebner | 396/22 |
| 5,159,367 | 10/1992 | Fusi | 396/4 |
| 5,481,439 | 1/1996 | Goto | 362/5 |
| 5,604,550 | 2/1997 | White | 396/4 |
| 5,717,958 | 2/1998 | Oka et al. | 396/2 |
| 5,778,258 | 7/1998 | Zamoyski | 396/2 |

*Primary Examiner*—Alan Cariaso
*Attorney, Agent, or Firm*—Alfred Walker

[57] ABSTRACT

A self-contained photography studio apparatus for photographing at least one subject comprising means to support and spatially orient the subject to be photographed, means for illuminating said subject so as to provide uniform illumination and substantially eliminate shadows, and means for controlling the temperature on and in the vicinity of said subject, wherein each of the recited means is integral, and a method for using the apparatus.

13 Claims, 1 Drawing Sheet

SELF-CONTAINED PHOTO STUDIO LIGHTING APPARATUS

This application is a continuation of provisional application Ser. No. 60/020,135 filed Jun. 20, 1996.

BACKGROUND OF THE INVENTION

1. Field of the Invention

This invention relates to a self-contained photographic studio apparatus which provides means for lighting, cooling, positioning and presenting two and three dimensional photographic subjects.

2. Description of the Related Art

Conventional photographic techniques involve substantial preparation prior to taking photographs of the desired subject. Such preparation includes the positioning and adjustment of lighting stands and lighting sources, wiring of camera, lighting, cooling and other equipment, placement of cooling fans, movement and positioning of the subject, choice and placement of backgrounds, and choice of lighting filters and masks. The result is that time spent by the photographer preparing for a photograph is significant, and competes with time spent by the photographer composing and taking photographs.

The equipment needed to operate a photographic studio, for instance, lighting, lighting rigging, fans, backdrops, filters, masks, reflectors, etc., is costly when purchased separately. Further, significant planning is required on the part of the photographer to ensure that the various equipment components function in a complementary manner in the studio.

Lighting systems are known which uniformly disperse light onto a desired subject or a desired surface or portion thereof. U.S. Pat. No. 3,690,242 relates to a photographic assembly which includes an inner surface which supports the subject to be photographed and rotates relative to an illuminating projector supported upon a stationary outer surface. This apparatus does not include a cooling system, reflective surfaces, diffusers and other related equipment. Moreover, the features present in this invention require significant adjustment, and the apparatus is unwieldy and not self-contained as that term is commonly understood.

U.S. Pat. Nos. 4,475,146 to Wally, Jr., 5,067,049 to Milaine, and 5,077,640 to Butler, Jr., all relate to photographic lighting apparatus. The inventions have limited features which relate only to lighting, and in each case require significant adjustment or preparation prior to use.

OBJECTS OF THE INVENTION

It is an object of the present invention to provide a photography lighting apparatus which is entirely self contained.

It is an object of the present invention to provide a photography lighting apparatus capable of eliminating all shadows on a three-dimensional photographic subject.

It is a further object of the present invention to provide a single, self-contained apparatus which simultaneously lights, cools, orients and otherwise presents a photographic subject.

It is an object further still to provide a cost-effective photographic apparatus for lighting, cooling, orienting and otherwise presenting a photographic subject.

SUMMARY OF THE INVENTION

The invention relates to a photography apparatus which provides uniform illumination for photographing or digitally imaging photographic subjects, including three-dimensional objects or flat arts, without casting unwanted shadows or heat on the subject. A complete photo studio lighting system 10 with built-in fixed light source 12 is illustrated in the attached FIG. 1. The self contained photo studio lighting is a complete system with built-in features such as: fixed lighting; light diffuser panel 14; background insertion 16; one or more masks for creating lighting effects 30; turntable 18 for rotating the subject being photographed or imaged; and, translucent turntable base 20 for eliminating bottom shadows. The main housing 28 inner lining is made of special panels which spread the light evenly and reflect it back with minimal loss. A built-in forced air cooling system removes heat (via electric fans, such as 22) keeping the inner chamber of the photo studio apparatus at room temperature.

For purposes of this invention, the term "photography" refers not only to color and black and white still photography, but also refers to moving picture photography and videography, to digital imaging techniques, and to any other known or developed imaging techniques.

DESCRIPTION OF PREFERRED EMBODIMENTS

Figure 1:
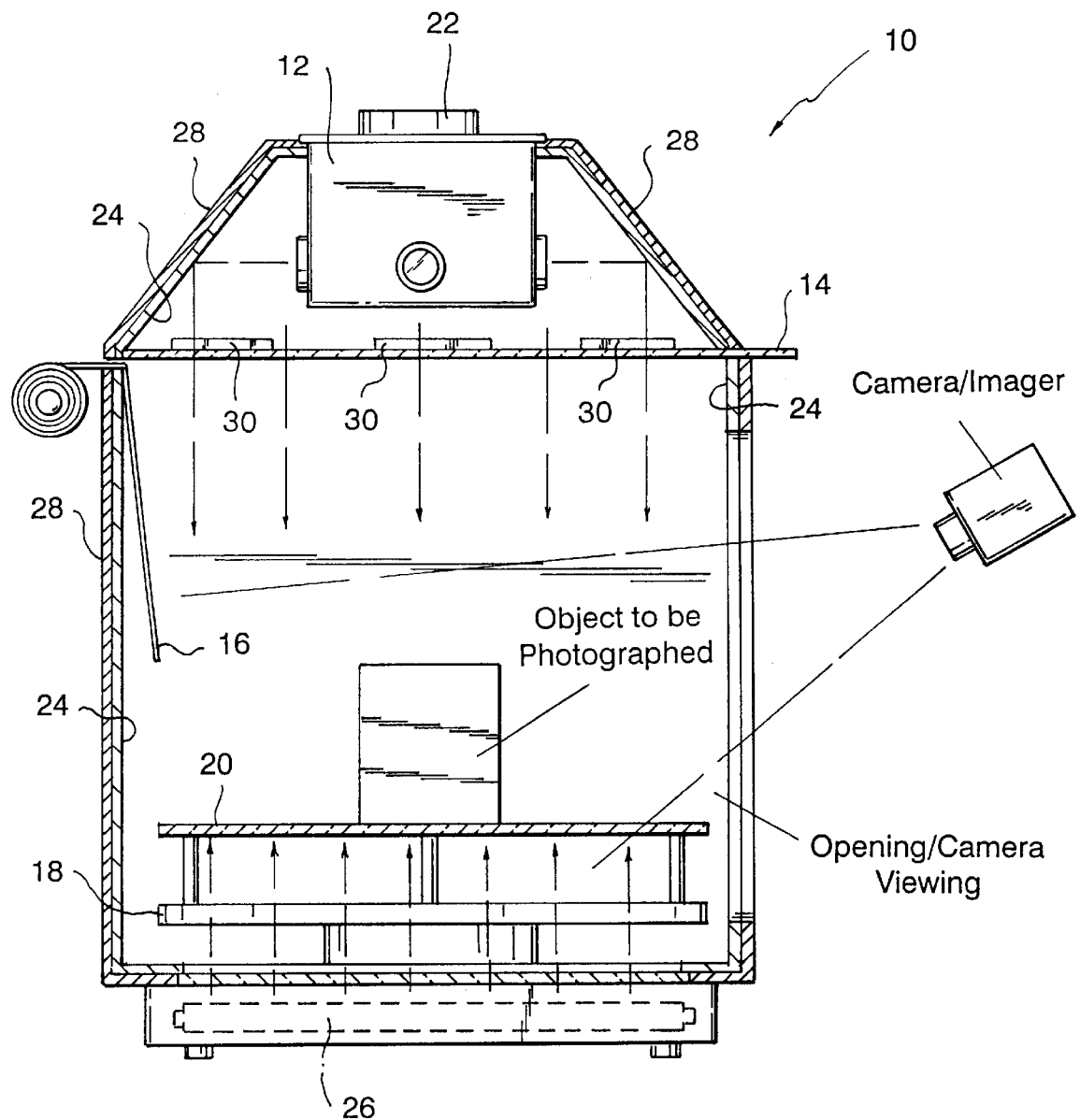

Light Source 12:

Lighting is accomplished by using one or multiple lamps. The light source 12 can be of a continuous type or an electronic flash. Built-in is a forced air cooling system which removes the heat from the light source housing therefore pulling cool air in from the opening of the main housing 28 into the light source housing over the lamps and exhausting it out through the top of the main housing 28.

Turntable 18:

The subject to be photographed can be positioned by rotating the turntable to get the best orientation prior to taking a photograph or Digital Photography scan. The turntable revolves around its axis 360 degrees and can be manually rotated clockwise or counter clockwise. The turntable may be motorized and remotely controlled so that the operator can judge for best positioning while looking through the view finder of a camera or at a video monitor.

Translucent Base 20:

The translucent base 20 which sits above the turntable top provides bottom illumination, if needed, therefore eliminating unwanted shadows cast by subjects, for example subjects having undercut bases or protuberances. The translucent base is optionally part of the rotating turntable.

An optional backlight 26 is positioned below the translucent base to enhance illumination below the subject.

Backgrounds 16:

A built-in access slot allows the insertion of a wide variety of photographic background materials to suit the subject.

Diffuser 14:

The diffuser 14 spreads the light uniformly and minimizes "hot spots". It slides in its own tracks through the front of the main housing 28, in addition, the diffuser absorbs Ultra Violet Rays which prevents them from interacting with the subject to be photographed or imaged.

Reflective Panels 24:

The reflective panels are made of special material that diffuse light evenly and reflect it back with minimal losses.

What is claimed is:

1. A self contained photography studio apparatus for photographing one or more subjects comprising a housing, said housing comprising a light box, said housing comprising means for supporting said subject, said supporting means being integrally attached within said housing, said supporting means further comprising movement means for user adjustment for spatially orienting said subject within said housing, means for illuminating said subject, said illuminating means being attached within said housing for providing light for effective substantially shadow-less illumination of a subject to be photographed, means for controlling the temperature on and in the vicinity of said subject to be photographed, said temperature control means being attached within said housing, wherein said supporting means, said spatially orienting means, said illuminating means, and said controlling means are cooperatively attached within said housing; and, said studio apparatus further having means for presenting a substantially shadow-less photographic subject to be photographed, said presenting means comprising said illuminating means providing light to said subject within said housing and said housing having an inner lining of reflective panels diffusing reflected light evenly while reflecting said light back with minimal losses.

2. A self-contained photography studio lighting apparatus for photographing one or more subjects comprising a housing, said housing comprising a light box, said housing means comprising a rotatable turntable, said turntable being integrally attached within said housing, said turntable further comprising movement means for user adjustment for spatially orienting said subject within said housing, said housing further comprising at least one light source, and at least one reflective surface, said combination of said at least one light source and said at least one reflective surface comprising illuminating means for effective substantially shadow-less illumination of a subject to be photographed, said housing further comprising a cooling system and at least one light diffuser, wherein said turntable, said at least one light source, the at least one reflective surface, said cooling system and said at least one light diffuser are cooperatively attached within said housing, and, said studio apparatus having means for presenting a substantially shadow-less photographic subject to be photographed;

said presenting means comprising said light source providing light to said subject within said housing, and said housing having an inner lining of reflective panels diffusing reflected light evenly while reflecting said light back with minimal losses.

3. A self-contained photography studio lighting apparatus for photographing one or more subjects comprising a housing, said housing having (a) a rotatable turntable, said turntable being integrally attached within said housing, said turntable further comprising movement means for user adjustment for spatially orienting said subject within said housing, said housing further comprising (b) at least one light source, and (c) at least one inner lining reflective surface, said combination of said at least one light source and said at least one inner lining reflective surface comprising illuminating means, said illuminating means being attached within said housing for effective substantially shadow-less illumination of a subject to be photographed, said housing further comprising (d) a cooling system and (e) at least one or light diffuser, cooperatively attached within said housing, wherein said turntable comprises a base, said turntable base being at least partially translucent, said at least one light source being fixed relative to said apparatus, said cooling system comprises at least one electric fan and wherein said apparatus further comprises a photographic background.

4. A self-contained photography studio lighting apparatus for photographing at least one subject comprising a housing, said housing having (a) a rotatable turntable for user adjustment of said at least one subject, (b) at least one light source, illuminating said at least one subject within said housing, (c) at least one reflective surface, reflecting light within said housing, (d) a cooling system and (e) at least one light diffuser, wherein each component (a) through (e) is cooperatively attached within said housing, wherein said turntable comprises a base, said turntable base being at least partially translucent, said at least one light source being fixed relative to said apparatus, said cooling system comprising at least one electric fan and wherein said apparatus further comprises a photographic background, whereby said at least one light source provides uniform illumination of said at least one subject, whereby shadows are substantially eliminated on and in the vicinity of said at least one subject.

5. The apparatus defined in claim 3, further comprising one or more lighting effect masks being arranged as part of said photography studio lighting apparatus.

6. A self contained photography studio lighting apparatus for photographing at least one subject comprising a main housing, said main housing having a rotatable turntable, at least one light source, at least one reflective surface, a cooling system and at least one light, diffuser, wherein said turntable, said at least one light, source said at least one reflective, surface, said cooling system, and said at least one light diffuser are coupled to said main housing, said studio apparatus having means for presenting a substantially shadow-less photographic subject to be photographed, said presenting means comprising an inner lining of reflective panels diffusing light evenly while reflecting light back with minimal losses.

7. The apparatus as defined in claim 3, wherein said light source comprises continuous lighting.

8. The apparatus as defined in claim 3, wherein said light sources comprises electronic flash lighting.

9. The apparatus as defined in claim 3, wherein said rotatable turntable is motorized.

10. The apparatus as defined in claim 6 wherein said main housing includes a slot for inserting and removing said photographic background.

11. The apparatus as defined in claim 3, wherein at least one of said one or more diffusers is removable.

12. An assembly kit which forms a self-contained photography studio lighting apparatus for photographing at least one subject when assembled, said assembly kit comprising a housing having a rotatable turntable, at least one light source, at least one reflective surface, a cooling system and at least one light diffuser, wherein said turntable, said at least one light source, said at least one reflective surface, said cooling system, and said at least one light diffuser are cooperatively arranged within said photographing studio lighting apparatus when said assembly kit is assembled, said studio apparatus having means for presenting a substantially shadow-less photographic subject to be photographed;

said presenting means comprising said light source providing light to said subject within said housing, and said housing having an inner lining of reflective panels diffusing reflected light evenly while reflecting said light back with minimal losses.

13. A method of photographing a three dimensional subject comprising the steps of:

placing said subject into a self-contained photography studio lighting apparatus comprising a housing, said housing having a rotatable turntable, at least one light, source at least one reflective surface, a cooling system and at least one light diffuser, wherein said turntable, said at least one light, source, said at least one reflective surface, said at least one cooling system, and said at least one light diffuser are cooperatively attached within said housing of said photographing studio lighting apparatus, photographing said subject, and providing a means for presenting a substantially shadow-less photographic subject to be photographed, said presenting means comprising the steps of:

providing light from said at least one light source to said subject within said housing, and subjecting said light within said housing to an inner lining of reflective panels diffusing reflected light evenly while reflecting said light back with minimal losses.

* * * * *